(12) United States Patent
Rezakhany

(10) Patent No.: US 11,890,409 B1
(45) Date of Patent: Feb. 6, 2024

(54) METHODS OF CURING EARLY STAGES OF, AND PREVENTING, UPPER RESPIRATORY INFECTIONS AND APPLICATORS THEREFOR

(71) Applicant: Saeed Rezakhany, San Jose, CA (US)

(72) Inventor: Saeed Rezakhany, San Jose, CA (US)

(73) Assignee: Saeed Rezakhany, San Jose, CA (US)

( * ) Notice: Subject to any disclaimer, the term of this patent is extended or adjusted under 35 U.S.C. 154(b) by 0 days.

(21) Appl. No.: 16/687,688

(22) Filed: Nov. 19, 2019

(51) Int. Cl.
*A61M 11/00* (2006.01)

(52) U.S. Cl.
CPC ... *A61M 11/007* (2014.02); *A61M 2202/0007* (2013.01); *A61M 2210/065* (2013.01); *A61M 2210/0612* (2013.01); *A61M 2210/0618* (2013.01)

(58) Field of Classification Search
CPC ........ A61M 11/007; A61M 2202/0007; A61M 2210/0612; A61M 2210/0618; A61M 2210/065
See application file for complete search history.

(56) References Cited

U.S. PATENT DOCUMENTS

| | | | | |
|---|---|---|---|---|
| 5,669,530 A | * | 9/1997 | Cichon | B05B 11/0013 222/153.09 |
| 2002/0158089 A1 | * | 10/2002 | Mehta | A61M 3/0262 222/420 |
| 2006/0110328 A1 | * | 5/2006 | Cagle | A61M 15/08 424/45 |
| 2010/0114016 A1 | * | 5/2010 | Gallo | A61H 35/04 604/73 |
| 2013/0298902 A1 | * | 11/2013 | Denton | B05B 1/3436 128/200.14 |
| 2021/0308436 A1 | * | 10/2021 | Liu | A61K 36/886 |

* cited by examiner

*Primary Examiner* — Steven O Douglas
(74) *Attorney, Agent, or Firm* — Edison Law Group

(57) ABSTRACT

Methods for curing early stages of, and preventing upper respiratory infections and applicators therefor are disclosed. One embodiment of the invention comprises using an applicator capable of generating a mist with the same predetermined effective formula concentration and average droplet size but at two flow volume levels. In accordance with the method of the invention, the flow volume is alternated between high and low flow levels as the applicator is used to treat the entire upper respiratory tract in a series of steps.

10 Claims, 2 Drawing Sheets

Figure 3:
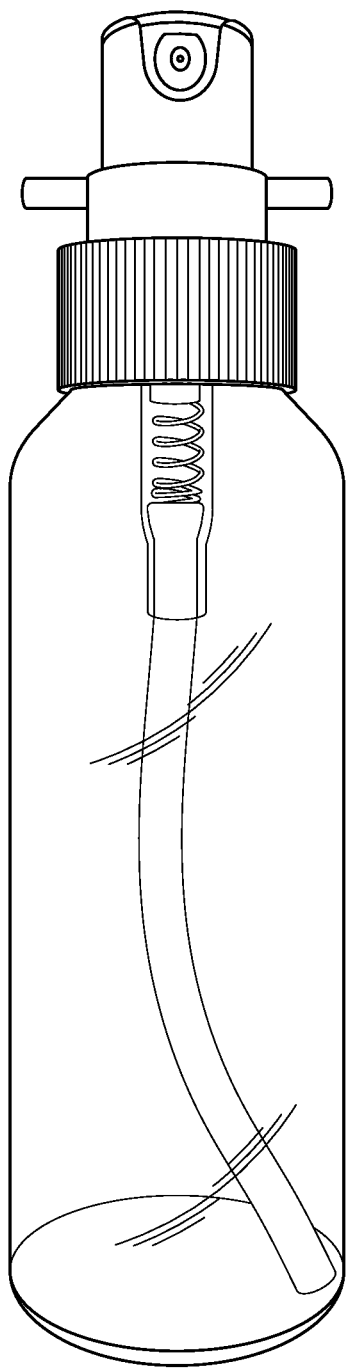

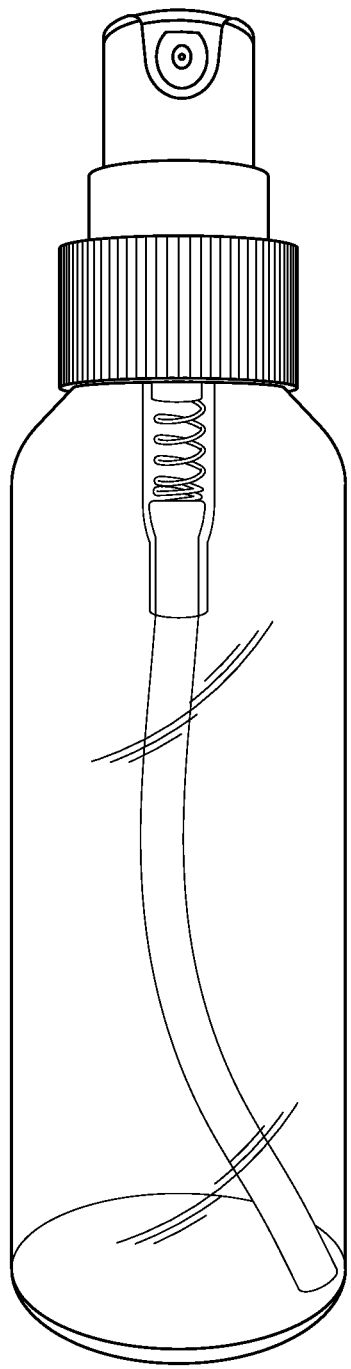
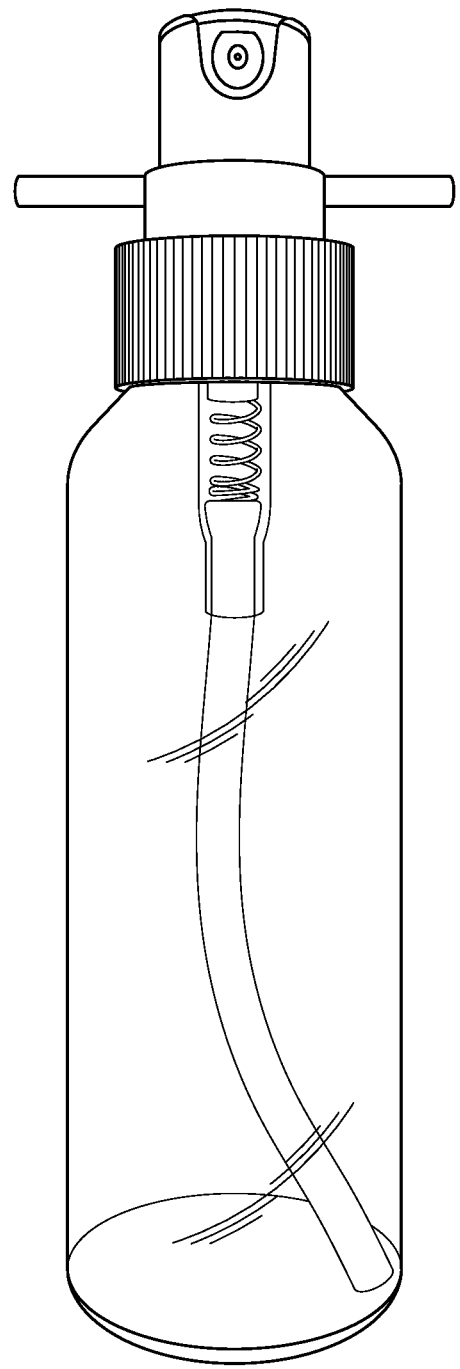
FIG. 1
PRIOR ART
FIG. 2
PRIOR ART

METHODS OF CURING EARLY STAGES OF, AND PREVENTING, UPPER RESPIRATORY INFECTIONS AND APPLICATORS THEREFOR

FIELD OF THE INVENTION

One or more embodiments of the present invention relate to curing of early stages of upper respiratory infections and prevention thereof.

BACKGROUND

Respiratory infections, particularly upper respiratory infections ("URIs") are very common and cause substantial suffering and hundreds of millions of dollars of economic loss every year. The majority of the pathogens contributing to upper respiratory tract infections are spread through air and through direct contact by touching of hands to infected surfaces and then touching hands to eyes, nose, or mouth. The nasopharynx, nasal passages, and sinus cavities all play an important role in filtering and housing the majority of these pathogens. No effective, easy to use, and widely accepted cure, treatment, remedy, and particularly no prevention has been found for upper respiratory infections. Stores are full of products that are alleged to reduce the severity of symptoms after infection has already developed. Numerous "home remedies," homeopathic products and treatments, and the like also exist. Many of these products offer little more than a placebo effect treatment, and the patient basically eventually fights the infection using internal infection-fighting resources. Vaccines exist for influenza. These are typically highly specific to a particular organism and must be newly developed each year for the strain or strains prevalent that year. Prescription antiviral medicines are also available to treat influenza, although questions about effectiveness, the cost, need for a prescription, and associated time delays before beginning treatment have prevented the widespread use of such medicines. Certain generally recommended hygiene practices can reduce the spread of URIs. These include washing hands frequently and thoroughly with soap and water; washing face, nose, eyes; not touching dirty hands to the eyes, nose, ears, mouth, and face; resting well; eating well; and exercising. At various times in the past, oral rinses (mouthwashes) have also been suggested to be beneficial for remedying some of the cold symptoms. However, such recommendations seem to have been merely suggestions based on the antiseptic properties of oral rinses, and have never been researched and developed to claim or substantiate prevention or cure, and thus do not appear on current products.

SUMMARY OF THE INVENTION

Methods for curing, early stages of, and preventing upper respiratory infections and applicators therefor are disclosed. One embodiment of the invention comprises using an applicator capable of generating a mist with the same predetermined concentration and average droplet size of an effective formula in liquid form, capable of rendering ineffective a pathogen which has recently infected the upper respiratory tract, but at two volume levels by having a mist sprayer mechanism with two spray volume settings, one for spraying a predetermined higher spray volume of the mist and one for spraying a predetermined lower spray volume of the mist, with the sprayer set at higher spray volume, to spray a predetermined amount of the mist to the mouth and throat of the infected human, then exhaling before inhaling such that the concentrated mist and vapor mixture is gently forced along with exhaled air from the throat through the nasopharynx and the nasal passages of the human, then while keeping the sprayer setting at the higher level, again spraying a predetermined amount of the mist to the throat area, then this time inhaling such that the mist is gently forced along with inhaled air through the larynx, over the vocal cords, and through the trachea to the lungs. The sprayer mechanism of the applicator is then set to the lower spray volume setting, and then the mist is sprayed at and near each of the outer nostrils of the human while inhaling such that the concentrated mist is gently forced into each of the nasal passages including the nasal cavities. Then, with the sprayer still set at the lower spray amount, a smaller, predetermined amount of the mist is applied on one of the fingers, leaving only a residual amount of liquid on the finger, then rubbing this residual liquid on the base of the eyelashes from one corner of each eye to the other corner while making sure that the eyelids, eyelashes, and eye corners are all externally dry and the eyelids are closed. The method should be applied soon after the human feels one or more minor symptoms as a result of a just recent (early stages of) upper respiratory infection by a pathogen, to render it ineffective. The entire method, except the rubbing of the effective formula at the base of the eyelashes which is repeated only a few times during a 24 hour period immediately after the initial infection, is repeated at least every half an hour until the human feels the effects of the pathogen infection no longer exist. This method can also be applied without existence of any symptoms, as a preventive measure against upper respiratory infections. As such it should be applied soon after the human comes in contact with other possibly infected humans, or, without any contact with infected persons, during the upper respiratory infection season, or during an upper respiratory infection outbreak, and it should be repeated a plurality of times during a 24 hour period. In curing mode, the method is performed immediately, but no more than about one hour after the human experiences the first minor symptom and before the onset of the first major symptom of infection of the respiratory tract.

BRIEF DESCRIPTION OF THE PHOTOGRAPHS

Some embodiments of the present invention are illustrated as an example and are not limited by the accompanying photographs, in which:

FIG. 1—a photo showing a typical mist sprayer bottle with a finger sprayer pump.

FIG. 2—a photo showing a typical mist sprayer bottle fitted with a double button pump actuator movement restriction mechanism in a not pushed in (nonrestrictive) mode.

FIG. 3—a photo showing a typical mist sprayer bottle fitted with a double button pump actuator movement restriction mechanism in a pushed in, reduced mist flow mode.

DETAILED DESCRIPTION

The Method Upper respiratory infections ("URIs") such as the common cold and influenza (the "flu") are generally preceded by one or more of a number of minor symptoms such as minor headaches, minor eye aches, minor ear aches, minor sore throat, minor body ache, minor nasal congestion, slight runny nose, minor cough, slight itching or scratchiness in the throat, itchiness in the ear, minor hoarseness, roughness in the eyes when moving the eyes or when blinking, sneezing, minor chills or shivers at normal room temperature, feeling abnormally warm at normal room temperature. These symptoms are characterized here as "minor" in the sense that they are just barely detectable and felt by the affected individual, they have typically just begun to be felt within the last hour or so, and they do not yet interfere significantly with normal daily activities. People generally ignore these symptoms, hoping they will just go away, or thinking that they may be caused by a minor allergy or irritation from dust or similar external cause. They wait for symptoms to develop into something more serious before beginning treatment. These symptoms can be called "major symptoms." Examples include sore throat, fever, muscle aches, serious headache, etc. These symptoms are characterized here as "major" in that they cause significant discomfort to the affected individual, persist for an extended period of time (hours to days or even weeks), cause a general feeling of illness, and interfere with normal daily activities including work, play, and sleep.

Treatment options for URIs are very limited. A variety of over-the-counter remedies are available, most of which have limited efficacy, and most URIs are basically allowed to run their course until the body's defense mechanisms eventually succeed in fighting off the infection. The present invention is directed to adapting some of the available over-the-counter products, specifically an oral rinse product as one embodiment of an effective formula, to treatment before a URI has fully developed. This treatment, if practiced according to the methods disclosed herein, has surprisingly been found to consistently cure the minor symptoms and prevent the development of major symptoms of URIs.

An important aspect of the present invention is the commencement of treatment at the earliest possible time as soon as even one of the minor symptoms is felt. The human body is equipped with organs, such as the tonsils and the nervous system, that give early warnings about the invasion of the respiratory tract by pathogens. This early warning initially produces minor symptoms that people tend to ignore. The inventor has discovered, however, that treatment leading to cure advantageously begins within the first hour or so from the onset of the first minor symptom. If one waits longer, then it can become progressively more difficult to prevent the development of the major symptoms. The goal is to render ineffective the pathogen(s) causing the infection as soon as their presence is detected and before they have a chance to multiply significantly. The method becomes less effective or ineffective if treatment is delayed until the onset of the first major symptom.

According to one or more embodiments of the present invention, an over-the-counter oral rinse or mouthwash is used as one embodiment of an effective formula. This is generally an anti-microbial solution. Reported "active" ingredients vary from product to product. A typical product includes one or more of thymol, eucalyptol, methyl salicylate, menthol, and iodine. Most products also contain alcohol which can also be an "active" ingredient for use with the present invention. A specific example composition comprises "active ingredients" thymol 0.064%, eucalyptol 0.092%, methyl salicylate 0.060%, and menthol 0.042%; together with "inactive ingredients" water, alcohol 26.9%, benzoic acid, poloxamer 407, and caramel.

According to one or more embodiments of the present invention, immediately after detecting one or more of the minor symptoms described above, using the applicator described below, with the sprayer mechanism set at the higher spray volume setting, approximately 0.3 to 0.6 milliliters of the mist of the above effective formula should be sprayed to the mouth and throat area of the infected human.

The oral rinse should then be swished around the mouth and throat area several (three to five) times to thoroughly disinfect the entire oral cavity. Then, with sprayer mechanism still set at the higher spray volume setting, approximately 0.3 to 0.4 milliliters of the mist should be applied to the throat area. Then, without delay, by exhaling before inhaling, the concentrated mist should be gently forced along with the exhaled air from the throat through the nasopharynx to the nasal passages. Then, while still keeping the sprayer setting at the higher level, another approximately 0.3 to 0.4 milliliters of the above effective formula's mist should again be sprayed to the throat area, except this time by inhaling without delay, the mist should gently be forced along with inhaled air through the larynx, over the vocal cords, and through the trachea to the lungs. The sprayer mechanism of the applicator is then set to the lower spray volume setting, and then only approximately 0.03 milliliter of the mist is sprayed at and near each of the outer nostrils, while, without delay, inhaling such that the concentrated mist is gently forced into each of the nasal passages including the nasal cavities. Then, the "eye part" of the method should be performed: that is with the sprayer still set at the lower spray amount, approximately 0.03 milliliters of the mist should be sprayed on one of the fingers (first making sure the finger is thoroughly clean and dry, for example by making sure it has been thoroughly washed with soap and water and dried) and letting the excess liquid to drip, leaving only a residual amount of liquid on the finger. Then, this residual liquid should be rubbed on the eyelashes and on the base of the eyelashes from one corner of each eye to the other corner while making sure that the eyelids, eyelashes, and eye corners are all externally dry and the eyelids are closed, and no effective formula gets in the eye. If it does, simply rinse the eye with water. This "eye part" of the method should only be repeated a few (three or four) times during a 24 hour period, and only if clearly the eye irritation is attributed to upper respiratory infection.

During each application of the method above, the entire method including the eye part can be repeated two to three times, one right after the other, as a means of emphasis. Excessive repetition of the method during each application, particularly the eye part, in other words more than two to three times, should be avoided.

At some point, before, during, or after the above steps, if any phlegm is generated, it should be removed by properly coughing it out of the mouth and/or gently blowing the nostrils, and rinsing. Obviously any excess liquid from the method on and around the nose should be rinsed off.

After the above steps are complete, the excess oral rinse should be completely emptied out from the mouth. The ingredients are generally non-toxic to humans in the quantities typically used, thus leaving the minor residual amounts of the oral rinse in the oral cavity including throat area have been proven to the inventor to be harmless and even possibly beneficial as a means of continuation of benefitting from the germicidal effects of the oral rinse used.

If one or both of the nasal passages are congested and thus do not pass air easily, then the necessary exhalation and inhalation containing the effective formula's mist should be gently forced by blocking the other nostril. Also, the entire method, with the exception of the part for the eyes, should be repeated when the nasal cycle in each nasal passage shifts, or one of the passages, or both open up or become less congested. It has been observed by the inventor that the effectiveness of the method increases when it is applied as the cycle is shifting and right after the cycle shifts. Often the nasal cycle shifts, and/or the nasal passages' congestion condition changes, right after rising from sleep. Therefore, right after rising from sleep, it is a good time to apply the method. Of course, it is best to begin treatment before nasal passages become congested, but there are situations in which one or both of the passages may already be clogged due to anatomical blockages (e.g. deviated septum, or collapsed cartilages), natural nasal cycle, allergies, environmental irritants, or excessive delay before first treatment.

According to one or more embodiments of the present invention, the complete method described above, with the exception of the eye part, is repeated at least every hour, starting from the onset of the first symptom until at least four treatments after the last symptom is detected. This is the recommended minimum frequency and duration of treatment. If initial minor symptoms become more pronounced, then treatment frequency should increase to approximately every 20-30 minutes during waking hours. Also, if exposed to other infected persons such as family members, co-workers, classmates, etc. with known symptoms of a URI, or if there is a known URI epidemic (an upper respiratory infection outbreak) in progress, then the frequency of treatment can similarly be increased to approximately every 30 minutes during waking hours. Also as a general rule for applying the method, for increasing the effectiveness of the method, if a person infected with URI, wakes up in the middle of the night, the entire method should also be applied with the exception of the eye part. In the middle of the night the eye part of the method should be applied, only if an eye irritation attributable to URI exists.

It is important to mention here that in URI, the dynamics of progress of infection are different for different pathogens or groups of pathogens. The inventor has observed that some pathogens causing URI can invade the body and thus cause minor symptoms in minutes, while others will take hours or even a few days. As such, the need for immediacy of starting application of the method described here, after an infection occurs, and the frequency of the application of the method, all depend on the specific pathogen infecting the body. Fortunately, as described above since humans are equipped with organs to detect the early stages of infection AND the severity thereof (by having more symptoms and more severe ones), the frequency of treatment can be adjusted to suit the particular infection. However, as one embodiment of present invention, as it was stated above, the application of the methods of this invention should be started within one hour of detection of the first minor symptoms.

As a further preventive measure, during the cold and flu season, or during an upper respiratory infection outbreak, even if no symptom exists and no suspected exposure to infected persons has occurred, the method described above can be performed three to four times a day, once right after rising in the morning, midday at least once, preferably twice, a few hours apart, and once again before going to bed at night.

Also, during the cold and flu season, or during an upper respiratory infection outbreak, within one hour after meeting with people or traveling through crowded places, the method can be performed, again as a preventive measure.

If the duration of exposure (for example, during travel or a public meeting) is longer than about two hours, then the method can advantageously be performed at least once during exposure and again after exposure. If it is suspected that specific exposure to an infected person is occurring, then the method can be performed approximately every 30 minutes throughout the exposure.

The 0.3-0.6 ml of the effective formula is an approximate range suitable for a healthy adult of medium size. The amount and repetitions can vary with the age and size of the person, as well as with other factors such as tolerance for the ingredients in the oral rinse.

There are two important features of the above-described methods that are not present in any prior art description (with the exception of the reference patent indicated at the beginning of this application) of the use of oral rinses. One is the use for the prevention of URIs by treating before any major symptoms develop. The second is the treatment of the entire respiratory system including the mouth, nose, nasal passages, nasopharynx, larynx, trachea, and lungs with either the liquid or concentrated mist from the oral rinse. This treatment of the entire respiratory system is never an accidental byproduct of any prior art methods nor is it inherent in gargling as it is commonly practiced or as recommended by manufacturers of oral rinse products. The current focus of advertising and product literature for oral rinses is on oral and dental health, treating such conditions as gingivitis and halitosis (bad breath). Directions do not ever mention anything about generating a mist and passing it throughout the air passages, focusing instead on treating just the mouth with the liquid product. It requires the novel method steps of the present invention embodiments to adequately treat the entire respiratory system with concentrated mist.

Similarly, other spray or inhalant products in the market are primarily for temporarily relieving the existing symptoms. For example, minor sore throat is relieved via use of analgesic compounds, or nasal air way congestion via decongestants and/or anti-inflammatory formulas. None of these spray or inhalant products makes any claims regarding cure or prevention of upper respiratory infections, the way it is done in this invention.

Although, the methods of the present invention, as described above, are focused on the prevention of the development of any major symptoms, in accordance with one or more embodiments of the present invention, a URI which has progressed past the minor symptom stage can still be beneficially treated to reduce the severity and duration of the major symptoms and the prevention of secondary infections. The recommended treatment frequency in this case is the same as for a person exposed to other infected individuals, i.e., for a few days, every 30-60 minutes during waking hours, and if awaken in middle of the night.

An infected person should not continue the methods of this invention indefinitely. Usually within 24 to 48 hours of the application of the above methods, the infected individual should see significant abatement of the minor symptoms. The inventor has experienced that, if the minor symptoms don't disappear or abate in a few days, they usually tend to get worse. If the symptoms do get worse, one should seek medical attention from a medical doctor, and with the consent of the medical doctor the patient should continue the methods of this invention for a few more days to reduce the severity and duration of the major symptoms and the prevention of secondary infections.

It is of extreme importance to mention here that, by no means the inventor is claiming to have invented a panacea for all respiratory infections. Only common cold and influenzas have been tested. Having said this, while testing has been conducted with regard to common URIs, the methods of the present invention can also be beneficial (curative and preventive) for early stages of many, if not all, other types of respiratory, nasal, and oral infections.

The methods of this invention should not be used as a substitute for other established procedures known to benefit health and prevent the spread of respiratory infections.

These other procedures include washing hands frequently and thoroughly with soap and water; washing face, nose, eyes; not touching dirty hands to the eyes, nose, ears, mouth, and face;

resting well; eating well; exercising when feeling well; and not exercising or doing major physical activities when infected with URI evident by presence of minor symptoms described here. The methods presented here should be used in conjunction with these other good health habits.

At this point, it is informative to share some of the inventor's experiments with the alternative uses of the present invention. For example, the inventor has observed that some of the headaches labeled "migraine", have responded favorably to the application of the present invention's methods. Also minor infections of the mouth, the eyes, and the nose have responded favorably to the treatments of the above methods. That is, it makes quite a lot of sense to state that since the methods of the present invention are effective on curing early stages of common URI's, they can as well be effective on curing and thus preventing early stages of, at least some of, other minor oral, nasal, and respiratory infections, being bacterial or viral. An example might be HSV type 1 (Herpes Simplex Virus, type 1).

The Applicator

One embodiment of the applicator is a modification of the commonly used consumer mist sprayers capable of generating fine mist used in fragrance, personal, and pharmaceutical applications, with finger pump sprayer or trigger pump sprayer with the double one way valve (check valve) mister mechanism. The modification comprises of a mechanism to reduce the mist (spray) flow volume. The pump modification can be implemented in any of the following ways:

1—According to one embodiment of the applicator for the present invention, the mist sprayer mechanism comprises a compound spray head consisting of two independent spray heads (nozzle, check valve—one way valve—and other parts) each having a different spray flow volume amount and thus, possibly different mist (droplet size) characteristic, but all having approximately, on the average, a diameter of 50 to 150 micrometers. The liquid flow supply line connected to the pumping mechanism is attached to the desired spray head as needed, by rotating the line head to align it with the desired spray head. Detailed drawings and dimensions will be provided.

2—According to another embodiment of the applicator for the present invention, the mist sprayer mechanism has the same check valve (one way valve) mechanism, however, two different end nozzles, by simply rotating the desired nozzle to align with the check valve and supply line mechanism. Detailed drawings and dimensions will be provided.

3—According to still another embodiment of the applicator for the present invention, the mist sprayer mechanism comprises a piston (barrel) movement blocker (a double button pump actuator movement restriction mechanism): In this design, the movement of the piston (pump actuator) in the cylinder of the pump mechanism is reduced (restricted) by blocking and therefore reducing (restricting) the range of movement of the piston, by introducing a stop rod in the path of the piston. Photos of a regular finger pump sprayer (FIG. 1), the same sprayer fitted with the stop rods in the open (nonrestrictive) mode (FIG. 2), and with the stop rods pushed in (restricting) mode (FIG. 3) are provided. Detailed drawings of the pump modification along with dimensions will be provided. The stop rod mechanism comprises push to engage and push again to disengage spring loaded rod mechanism implemented at the base of the cylinder (piston's housing or piston's jacket) at a location near the top of the jacket (FIG. 2) where, when the stop rod is engaged (pushed in) the restriction of the flow will be enough to produce only sufficient amount (volume) of the mist to meet the lower spray volume specification of this invention, for example 0.03 ml. In this design, the full range of piston movement and the restricted movement should produce the same average size droplets (about 50 to 150 micrometers). Only the volume (amount) of the spray mist generated will be different. Again all of the relevant, detailed drawings and dimensions will be provided.

4—According to still another embodiment of the applicator for the present invention, the mist sprayer of item 3 above is used, except the sprayer head has a cylindrical extension for ease of spraying the throat area. All of the relevant, detailed drawings and dimensions will be provided.

5—According to still another embodiment of the applicator for the present invention, a practical embodiment, but not accurate in terms of dosage, however, possibly the most economical in terms of production is simply a regular mist sprayer (FIG. 1). In this embodiment, when the lower level of mist is needed, the finger pump is simply pressed about a fraction of as much as one would press to get the full dose. Therefore, no modification of a regular mist sprayer is needed.

6—According to still another embodiment of the applicator for the present invention, the mist sprayer is a mini trigger pump with the trigger pumping mechanism modified to have two distinct spray flows. Two flow levels are implemented by having a restriction bar to prevent the trigger to travel the full course of motion for one spray. Detailed drawings and dimensions will be provided.

In all of the above designs, the mist sprayers described generate mists with droplet sizes ranging from 50 to 150 micrometers, dosage 0.1 to 0.2 ml per spray, reduced dosage about 0.03 ml. The mister sprayer bottles can be generally of the size 60 to 120 ml.

In a completely different embodiment of the methods of and applicator for the present invention, one can use an ultrasonic or regular (with an electric heating element) humidifier. In this embodiment the effective formula can be added to the water or poured in the medicine container (cup) of the humidifier. Then the person with URI, will place face, nose, and mouth in the path of the vapor coming from the humidifier and apply the method. The eye part of the method can be applied by placing the eye, while closed, for about 30 second in the path of steam/effective formula.

In another completely different embodiment of the methods of and applicator for the present invention, one can add the effective formula to the air conditioning system so that the effective formula would be dispersed in the air for either continuous supply of the effective formula, or for short durations of time throughout day and night. The effective formula is added to the air stream via an effective formula/air mixing chamber wherein the main air stream passes through and thus carries the effective formula fine mist. This embodiment can be particularly useful for where humans are meeting, in order to prevent spreading (transferring) of URI. The eye part of the method, if needed, maybe applied by a separate applicator similar to any of the ones described above.

What is claimed is:

1. A method for treating respiratory infections in a human patient using a misting applicator generating a mist from an oral rinse, the applicator having first and second spray volume settings to generate first and second misted spray quantities, the method comprising the steps of:
    setting the applicator spray volume level to said first spray volume setting and spraying the first quantity of the oral rinse into the patient's mouth and throat, the patient then swishing the oral rinse around the mouth before emptying the first quantity of oral rinse from the mouth;
    spraying the first quantity of the oral rinse only to the patient's throat area;
    having the patient immediately exhale said first quantity before inhaling such that the first quantity of the oral rinse is gently forced along with exhaled air from the throat area through said patient's nasopharynx and nasal passages;
    spraying of the first quantity of said oral rinse again only to the throat area; immediately inhaling such that the first misted quantity is gently forced along with inhaled air through or over the patient's larynx, vocal cords, and trachea to the patient's lungs;
    setting the applicator spray volume level to said second spray volume setting and spraying said second quantity of the oral rinse near and at each of the patient's nostrils while inhaling; and,
    spraying said second quantity of the oral rinse at each of the patient's eyes and eyelashes.

2. The method of claim 1 wherein the method is started within about one hour after said patient experiences one or more of a set of minor symptoms including headaches, eye aches, ear aches, sore throat, body ache, nasal congestion, runny nose, cough, itching or scratchiness in the throat area, itchiness in the ear, hoarseness, roughness in the eyes when moving the eyes or eyelids, sneezing, chills or shivering at normal room temperature, or feeling abnormally warm.

3. The method of claim 1, wherein the method is started before onset of major symptoms of infection of the respiratory tract.

4. The method of claim 1, wherein the method is repeated at intervals of four to six hours during waking hours until at least two treatments after the last minor symptom is experienced.

5. The method of claim 1, wherein the method is repeated at intervals of about 20-60 minutes during waking hours until at least four treatments after the last minor symptom is experienced and throughout any period during which the patient is exposed to an infectious environment.

6. The method of claim 1, wherein the method is performed four to five times per day during the cold and flu season, or during an upper respiratory infection outbreak.

7. The method of claim 1, wherein the method is performed within one hour after the human is exposed to an infectious environment.

8. The method of claim 1, wherein when the patient is exposed to an infectious environment for 2 or more hours and wherein the method is performed at least once during exposure and once afterwards.

9. The method of claim 1, wherein the method is performed approximately every 30 minutes while the patient is exposed to a person who is known to be infected with a respiratory pathogen.

10. The method of claim 1, wherein said oral rinse comprises one or more of thymol, eucolyptol, methyl salicylate, iodine, and ethanol.

* * * * *